(12) United States Patent
Pfau

(10) Patent No.: US 9,868,931 B2
(45) Date of Patent: Jan. 16, 2018

(54) METHODS AND AN APPARATUS FOR TRANSPORTING LIVE CELLS

(71) Applicant: James David Pfau, Oceanside, CA (US)

(72) Inventor: James David Pfau, Oceanside, CA (US)

( * ) Notice: Subject to any disclaimer, the term of this patent is extended or adjusted under 35 U.S.C. 154(b) by 11 days.

(21) Appl. No.: 14/821,729

(22) Filed: Aug. 8, 2015

(65) Prior Publication Data

US 2016/0040117 A1    Feb. 11, 2016

Related U.S. Application Data

(60) Provisional application No. 62/035,351, filed on Aug. 8, 2014.

(51) Int. Cl.
| | | |
|---|---|---|
| *C12N 1/04* | (2006.01) | |
| *C12M 1/00* | (2006.01) | |
| *C12N 1/16* | (2006.01) | |
| *C12N 1/20* | (2006.01) | |

(52) U.S. Cl.
CPC ............ *C12N 1/04* (2013.01); *C12M 45/22* (2013.01); *C12N 1/16* (2013.01); *C12N 1/20* (2013.01)

(58) Field of Classification Search
CPC ... C12N 1/04; C12N 1/16; C12N 1/20; C12M 45/22
See application file for complete search history.

(56) References Cited

U.S. PATENT DOCUMENTS

| | | | | |
|---|---|---|---|---|
| 5,635,344 | A * | 6/1997 | Garcia ............... | A01N 1/02 435/1.1 |
| 7,732,184 | B2 * | 6/2010 | Kringelum ........ | A23C 19/0323 426/232 |
| 2002/0019042 | A1 * | 2/2002 | Dicosimo .......... | C12N 1/04 435/252.1 |
| 2009/0145087 | A1 * | 6/2009 | Allen-Hoffmann .. | A01N 1/02 53/440 |

OTHER PUBLICATIONS

Def. for "on demand" Cambridge English Dictionary, available on-line at http://dictionary.cambridge.org/us/dictionary/english/on-demand, last accessed May 1, 2017.*
Nakasone et al. "Preservatin and Distribution of Fungal Cultures" 2004, in Biodiversity of Fungi: Inventory and Monitoring Methods, eds. Mueller, Bills & Foster, pp. 37-47.*

* cited by examiner

*Primary Examiner* — Teresa E Knight

(57) ABSTRACT

The invention provides improved methods and an apparatus for transporting a starter culture of living cells including fungi, bacteria, animal and plant cells. The methods and apparatus enable on-demand feeding and on-demand supply of nutrient gas resulting in increased cell viability and improved fermentations.

19 Claims, 4 Drawing Sheets

METHODS AND AN APPARATUS FOR TRANSPORTING LIVE CELLS

FIELD OF INVENTION

Fermentation uses the growth of microorganisms to convert a raw material into useful product. The best known fermentations convert grapes into wine and barley into beer. Fermentation is also used industrially for many important applications. All fermentations require an initial quantity of cells in order to efficiently transform the substrate. This initial quantity of cells is usually provided as a powdered starter culture which can be added directly to the fermentation tank. Although easy to handle, powdered starters contain large numbers of dead and dying cells leading to unreliable initial cell counts and frequently causing incomplete fermentations. Liquid starters have better initial cell count accuracy but still suffer from considerable cell death and often result in incomplete fermentations.

BACKGROUND OF THE INVENTION

Fermentation

The foremost application of fermentation is producing microorganisms for other fermentations. For example 2.8 million metric tons of Baker's yeast was produced in 2003 (Hui et al 2004). In addition to making bread, beer and wine, yeast is used to produce biofuel (Buijs et al. 2013); to produce enzymes (catalase, amylase, protease, pectinase, glucose isomerase, cellulose, hemicellulose, lipase, lactase); to produce recombinant proteins and small molecule drugs (insulin, HepB vaccine, interferon, granulocyte colony stimulating factor, artemisinin) (Hollenberg et al. 1997). Fermentation with penicillin mold produces antibiotics (cyclosporin A, gramicidin S, gibberellin, griseofulvin, lovastatin) (Madigan et al. 1997). Fermentation using *Lactobacillus* bacteria is used to make dairy products like yogurt, and for production of organic acids (lactic acid, acetic acid, formic acid, propionic acid) for food preservation (Madigan et al. 1997). Other organic acids can be derived by fermentation with other species of bacteria.

In all fermentations it is critical to match growth media which contains substrate to the live cells in use. All growth media must contain a carbon source, a nitrogen source, water, salts and micronutrients. Adding cells to growth media or a fermentation tank is known as pitching. For brewing beer typical pitch rates are between 6-24 million cells/milliliter. Once live cells begin feeding on substrate they proceed through stereotypical phases of growth consisting of the lag phase, the exponential phase, the stationary phase, and the death phase (Rolfe et al. 2012). The lag phase is the initial period when a starter culture is first introduced into growth media. The cells grow slowly as they adapt to the growth media but then grow rapidly in the exponential or log phase wherein the population size increases by orders of magnitude. As the available nutrients are consumed and metabolic products accumulate, growth decelerates and the population enters the stationary phase. Cell counts in the stationary phase are roughly constant because all the consumable carbon is gone, but prolonged storage results in cell death.

The efficiency of fermentation is directly related to the population of healthy cells present in the starter culture. Powdered or lyophilized starters are popular because many cell types are tolerant to dehydration and easily shipped. But the drying process damages or kills many cells by disrupting cell membranes and denaturing important proteins. Dried preparations are therefore unreliable as to the initial cell count. Dried starters are also easily contaminated by both fungus and bacteria. Dried starters frequently produce slow and incomplete fermentations that contain unwanted side products. Liquid starters are an improvement because they avoid dehydration and the resulting extended lag phase. However liquid starters still may exhibit considerable cell death in storage and transport and therefore arrive with unreliable initial cell counts. Liquid starters have these problems because shipped cells are sealed in air-tight containers in stationary phase media without any food source for extended periods. The resulting starter populations have many dead and dying cells upon arrival producing effective pitching rates below calculated pitching rates and poor quality fermentations.

Yeast Starters

Yeast are classified in the kingdom Fungi. Approximately 1500 species are known among which several are actively cultivated including *Saccharomyces*, *Pichia* and *Candida*. Individual yeast are 10 um in diameter on average. Yeast conduct ethanol fermentation anaerobically converting one mole of glucose into two moles of ethanol, two moles of $CO_2$ and two moles of ATP. Yeast strains have been bred and selected for favorable properties over thousands of years and there are now hundreds of commercially available strains.

Most baker's yeasts are *Saccharomyces cerevisiae*. Baker's yeast strains are selected for their ability to rapidly carbonate dough. A common form is "active dry" yeast that has been vacuum dehydrated and preserved with non-ionic detergent like sorbitan monostearate. Active dry yeast has a limited shelf life of several months when stored in a cool, dry place. Fresh baker's yeast is also available and unlike active dry yeast requires no proofing prior to use. Though it produces better bread, fresh yeast has a very short shelf life lasting no more than two weeks at 4° C. without decreased viability. Liquid starters are fresh yeast that remain in stationary phase liquid media. They have the longest shelf life of up to one year at 4° C. But depending upon the time of storage and conditions during shipping liquid starters also suffer from reduced viability and unreliable initial cell counts.

Most brewer's yeasts are also *S. cerevisiae* but usually slower acting varieties that produce fewer off-flavors and tolerate higher alcohol concentrations (Lam 2014, U.S. Pat. No. 8,394,622). Brewer's yeast starters are traditionally supplied in dry form but are increasingly available as liquid starters. Several liquid starters are known in the art but most are just volumes of concentrated yeast cells in sanitized plastic containers that are shipped on ice or with refrigeration. Another liquid starter packages yeast with an internal pressure-sensitive sac that releases malt nutrient upon impact. The added nutrient carbon allows shipped yeast to feed and grow anaerobically prior to addition to the fermentation tank. Such pre-fermentation feeding enhances yeast viability and gives improved results compared to other liquid starters and especially compared to dry starters. What is needed is an improved starter culture that provides a highly viable population of cells with an accurate initial cell count.

Bacterial Starters

*Lactobacillus* or lactic acid bacteria (LABs) are anaerobic, gram-positive, acid-tolerant, rod-shaped bacteria. LABs produce lactic and acetic acid as the metabolic end product of sugar fermentation. Species such as *L. casei*, *L. delbruecki* and *L. brevis* are commonly used in the food industry for production of cheese, yogurt, butter, buttermilk and kefir (U.S. Pat. No. 7,732,184) as well as for maturation of wine, pickle and sauerkraut production; and for curing meats such as salami, pepperoni and ham. LABs are also widely used as preservatives and souring agents. By producing lactic and acetic acid, LABs inhibit the growth of spoiling bacteria and fungus. Some LABs also produce bacteriocin proteins that further inhibit the growth of pathogens.

Mycorhizzae Starters

Mycorhizzae are specialized fungal cells that exist in a symbiotic relationship with plant roots. Many tons are applied to fields annually to improve crop yields and for soil remediation. Frequently used varieties include Ectomycorhizzal genera such as *Pisolithus* and *Rhizopogon*, and Endomycorhizzal genera such as *Glomus* and *Gigaspora*. Mycorhizzae promote plant growth by accumulating Phosphorous and other minerals from soil and transferring these essential nutrients to plants in exchange for photosynthesis derived glucose. Plants may feed up to 20% of photosynthetic sugar to the hyphal network and as much as 30-50% of plant minerals are taken up by the mycorhizzae.

Like yeast starters, most LABs and mycorhizzal starters are available as powder preparations. Though liquid starters of LABs and mycorrhizae are less prevalent, they offer all the same advantages over dried preparations that liquid yeast starters do. As with all liquid starters, the efficiency and completeness of fermentations depend upon the time of storage and conditions during shipping. What is needed are improved starter cultures for a range of organisms used in fermentation processes where the starter culture provides an accurate cell count of a population of highly viable, uncontaminated cells, and where the number of cells pitched matches the quantity of substrate available enabling efficient and complete fermentation.

RELEVANT ART

U.S. Pat. No. 8,802,421—Method of Propagating and Delivering Yeast: Discloses a modular multi-bag propagation unit for small-scale liquid yeast production.

EP 0143261—Packaging of Baker Yeast: Discloses a gas permeable bag that is hermetically sealed which allows fermentation to occur within the bag.

EP 2067686—Nobel-Transport Device for Cream Yeast: Discloses a tank mounted upon a wheeled trolley for transporting up to 1000 liters of cream yeast.

U.S. Pat. No. 8,394,622—Yeast strains for improved ethanol production: Discloses *Saccharomyces cerevisiae* strains that tolerate increased fermentation temperature, increase glucose levels and ethanol tolerance.

US 20140356879—Genes conferring tolerance to ethanol and high temperature for yeasts: Discloses eukaryotic genes that increase ethanol tolerance in *Saccharomyces cerevisiae*.

US 20060257529—Yeast compositions and starter cultures: Discloses yeast compositions in starter cultures comprised of Saccharomycetaceae and *Saccharomyces* in a dried preparation.

U.S. Pat. No. 6,942,962—Computer monitoring and control of fermentation: Discloses a process of fermentation monitoring which quantifies reacting chemicals using a cellular yield curve to create mass balance.

U.S. Pat. No. 4,832,968—Beverage Package and a Method of Packaging a Beverage Containing Gas in Solution: Discloses a container containing a hollow pod with restricted aperature that is filled with a gas saturated solution to produce a head of froth when opened.

EP 0747298—Method of inserting a gas-jetting capsule into a beverage can having a reduced diameter neck: Discloses means for attaching a gas capsule to the bottom of a can and means for filling the can that pressurizes the gas capsule.

UK 1266351—Improved Method of and Means for Dispensing Carbonated Liquids from Containers: Discloses a packaged beverage with a charge of gas in a subsidiary compartment for producing fine bubbles in the liquid.

U.S. Pat. No. 7,732,184—Liquid Starter Cultures Having Improved Storage Stability and Use Thereof: Discloses a liquid microbial starter culture that retains metabolic activity for extended periods by supplying a carbon source.

U.S. Pat. No. 3,117,009—Method and Apparatus for Producing a Starter Culture for Making Cheese and the Like: Discloses a culture processing cabinet for producing sterile starter cultures.

U.S. Pat. No. 3,483,087—Cheese Starter Culture: Discloses improved cheese starter cultures by culturing in buffered media with cooling.

U.S. Pat. No. 5,021,350—Process for inclusion of mycorrhizae and actinorrhizae in a matrix: Discloses a preparation of fungal cells in a polymer gel.

U.S. Pat. No. 4,327,181—Aerobic submerged fermentation of sporulating, ectomycorrhizal fungi: Discloses propagation of fungi in a liquid media with nutrients and a carrier for nucleating fungal growth.

US 20150040629—Novel Mycorrhizae-based Biofertilizer Compositions & Method for mass production & formulations of Same: Discloses an air-dried fungus fertilizer comprised of several mycorrhizae species including *Glomus, Gigaspora*, and *Scutellospora*.

U.S. Pat. No. 5,348,875 A—Production of alginase from *Enterobacter cloacae* M-1: Discloses a process for production of Enterobacteria and as a method for decomposing alginic acid.

U.S. Pat. No. 8,944,048 B2—Apparatus and methods of providing diatomic oxygen (o2) using ferrate(vi)-containing compositions: Discloses a methods of producing oxygen gas from powder.

U.S. Pat. No. 4,256,256 A—Multiple compartment pouch and method of making same: Discloses a container that holds discrete contents in discrete compartments.

US 20130301957 A1—Multi-compartment pouch with breakable inner compartment: Discloses a container that allows mixing of the contents of two discrete compartments within a single container.

REFERENCES CITED

Tymczyszyn, E., E. Effect of sugars and growth media on the dehydration of *Lactobacillus delbrueckii* ssp. *bulgaricus*. J Appl Microbiol. 2007 March; 102(3):845-51.

Carvalho, A., S. Effects of Various Sugars Added to Growth and Drying Media upon Thermotolerance and Survival throughout Storage of Freeze-Dried *lactobacillus delbrueckii* ssp. *Bulgaricus*. Biotechnology Progress Volume 20, Issue 1, pages 248-254, 2004.

Pericin, D. Production and some characteristics of beta-glucosidase in *Diaporthe (Phomopsis) helianthi*. Acta Microbiol Immunol Hung. 1995; 42(1):29-37.

Pardeep, K. Microbial glucoamylases: characteristics and applications. Critical Reviews in Biotechnology 2009 29:3, 225-255.

Wilson, W., A. Regulation of glycogen metabolism in yeast and bacteria. FEMS Microbiol Rev. 2010 November; 34(6):952-85.

Sivaramakrishnan, S. "a-Amylases from microbial sources—an overview on recent developments." Food Technol Biotechnol 44.2 (2006): 173-184.

Rolfe, M. et al. "Lag Phase Is a Distinct Growth Phase That Prepares Bacteria for Exponential Growth and Involves Transient Metal Accumulation." Journal of Bacteriology 194.3 (2012): 686-701.

Lam, F. H. et al. Engineering alcohol tolerance in yeast. Science 3 Oct. 2014: 346 (6205), 71-75.

Marschner, H. Nutrient uptake in mycorrhizal symbiosis. Plant and Soil. February 1994, Volume 159, Issue 1, pp 89-102.

Hermida, C., et al. Optimizing the enzymatic synthesis of beta-D-galactopyranosyl-D-xyloses for their use in the evaluation of lactase activity in vivo. Bioorg. Med. Chem. 15 (14): 4836-40. 2007.

Hui, Y. H., et al. Handbook of Food and Beverage Fermentation Technology. CRC Press 2004.

Buijs, N., A. Advanced biofuel production by the yeast *Saccharomyces cerevisiae*. Current Opinion in Chemical Biology. Volume 17, Issue 3, June 2013, Pages 480-488.

Madigan, M., T., et al. Production of recombinant proteins by methylotrophic yeasts. Current Opinion in Biotechnology Volume 8, Issue 5, October 1997, Pages 554-560.

Kirk, O. Industrial enzyme applications. Current opinion in biotechnology 13.4 (2002): 345-351.

Bourne, D., T., et al. β-Glucan and β-Glucanase in Brewing. Journal of the Institute of Brewing 76.4 (1970): 328-335.

Bachofen, R. Gas metabolism of microorganisms. Experientia. 15 Jun. 1991, Volume 47, Issue 6, pp 508-513.

Rosenfeld, E., et al. Oxygen Consumption by Anaerobic *Saccharomyces cerevisiae* under Enological Conditions: Effect on Fermentation Kinetics. Applied And Environmental Microbiology, January 2003, P. 113-121 Vol. 69, No. 1.

SUMMARY OF THE INVENTION

The present invention provides improved methods and an apparatus for shipping live cells. Non-limiting examples of live cells which may be shipped include fungal, bacterial, animal, and plant cells. Shipped cells may optionally be genetic mutants such that specific metabolic pathways are inactivated. In particular these improved methods and live cell shipping container enable on-demand feeding and on-demand supply of nutrient gas. On-demand feeding and supply of nutrient gas enables shipped cells to build up biochemical energy and essential nutrients for cell division prior to downstream fermentation. As a result cells shipped using the disclosed invention maintain high viability, provide an accurate cell count, avoid an extended lag phase following pitching, and deliver robust fermentative capacity.

In one aspect of the present invention an improved method for shipping live cells is provided by on-demand feeding. On-demand feeding allows live cells to replenish biochemical energy at the point of use prior to fermentation. The ability to engage in metabolic activity prior to fermentation increases the viable population of cells allowing for a more accurate initial cell count and therefore more predictable fermentations. In one non-limiting example on-demand feeding is enabled by providing a thermolabile enzyme-substrate pair consisting of polysaccharide and glycosidase. When the temperature of the shipping container reaches activating temperatures for the glycosidase enzyme, polysaccharide sugar molecules are depolymerized into smaller, mono and disaccharides that are available for consumption. Non-limiting examples of non-metabolizable carbon sources are one or a mixture of: Agarose, Alginic Acid, Amylose, Amylopectin, Cellulose, Chitin, Chitosan, Chondroitin Sulfates, Dextran, β-Glucans, Glycogen, Hemicellulose, Heparan Sulfate, Heparin, Hyaluronic Acid, Inulin, Isomaltose, Lactose, Lichenen, Pectins, Peptidoglycans, Pullulan, Starch, Trehalose, Xylan. Non-limiting examples of glycosidase enzymes appropriate to digest these carbohydrates or mixtures thereof are: Agarase, Alginate Lyase, α-Amylase, β-Amylase, Amyloglucosidase, β-Galactosidade, Cellulase, Chitinase, Chitosanase, Chondroitinases, Dextranase, Driselase, α-Glucosidase, Hemicellulase, Heparinases, Hyaluronidase, Inulinase, Isoamylase, Isomaltase, Lysozyme, Lyticase, Laminarinase, Pectinase, Pectolyase, Pectinesterase, Pullulanase, Xylanase.

In other non-limiting examples of on-demand feeding the thermolabile enzyme substrate pair may use an alternate carbon source such as lipid, protein, peptide, or nucleic acid sources or mixtures thereof and appropriately matched enzyme such as lipase, protease, nuclease or mixtures thereof. The enzyme used may optionally be a genetic mutant protein such that the enzyme may be used at higher or lower temperatures than non-mutant enzymes.

In another aspect of the present invention, an improved method for shipping live cells is enabled by providing nutrient gas on-demand. On-demand nutrient gas allows live cells to engage in respiration prior to use in fermentation. The ability to engage in respiration prior to fermentation enables cells to build up biochemical energy and essential nutrients for cell division and downstream fermentation (Rosenfed et al. 2003). Non-limiting examples of the nutrient gas supplied may be one or a mixture of: $O_2$, $N_2$, $H_2$, $CO_2$, $CH_4$, CO, NO (Bachofen 1991).

In a non-limiting example on-demand oxygenation is provided by including a gas canister within the shipping container that is opened by pulling upon a physical tether attached to a tear-away section in the gas canister.

In another non-limiting example on-demand oxygenation is provided by including a gas canister within the shipping container that is opened by pulling upon a physical tether attached to a plug in an orifice of the gas canister.

In another non-limiting example, on-demand nutrient gas is released from a gas canister within the shipping container by applying pressure to a puncture rod positioned adjacent to a pre-stressed section or thin-walled section of the gas canister.

In another non-limiting example, on-demand nutrient gas is released from the gas canister within the shipping container by applying pulling or pushing pressure to an arm attached to a door or latch on the gas canister.

In another non-limiting example, on-demand nutrient gas is released from the gas canister within the shipping container by use of a wireless receiver and battery which opens a solenoid valve in the gas canister.

In another non-limiting example, on-demand nutrient gas is released from the gas canister within the shipping container by use of a wireless receiver and battery which powers a piezo-electric valve in the gas canister.

In another non-limiting example on-demand nutrient gas may be supplied by connecting an external gas source to a valve on an external surface of the shipping container.

In another non-limiting example on-demand nutrient gas is released from the canister by opening the shipping container, wherein rapid depressurization causes a plug to be expelled from an orifice in the gas canister.

In another non-limiting example on-demand nutrient gas is released from the canister by opening the shipping container, wherein rapid depressurization causes a gas to escape from an orifice in the gas canister.

In another non-limiting example on-demand nutrient gas is supplied by a chemical reaction wherein two reactive powders are mixed together resulting in nutrient gas.

In another non-limiting example of the shipping container, all the interior surfaces are chemically sterilized.

In another non-limiting example of the shipping container, all the interior surfaces are coated with a non-stick surface to prevent shipped cells from adhering to the walls.

In another non-limiting example the shipping container may be insulated so that it is isothermic.

In another non-limiting example the shipping container may be opaque to protect cells from ultra-violet sources.

The present invention achieves its objects by providing methods and an apparatus for transporting live cells. The manners in which the invention achieves its objects and other objects which are inherent in the invention will become more readily apparent when reference is made to the accompanying drawings.

DETAILED DESCRIPTION OF THE INVENTION

Various embodiments of the invention are described in detail and may be further illustrated by the provided examples. As used in the description herein and throughout the claims that follow, the meaning of "a," "an," and "the" includes the plural reference unless the context clearly dictates otherwise. Also, as used in the description herein, the meaning of "in" includes "in" and "on" unless the context clearly dictates otherwise.

Throughout this specification and claims, the word "comprise," or variations such as "comprises" or "comprising" will be understood to imply the inclusion of a stated integer or group of integers but not the exclusion of any other integer or group of integers.

Terms used in this specification generally have their ordinary meanings in the art, within the context of the invention, and in the specific context where each term is used. Certain terms that are used to describe the invention are discussed below, or elsewhere in the specification, to provide additional guidance to the practitioner in describing the compositions and methods of the invention and how to make and use them. For convenience, certain terms may be highlighted for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms does not exclude the use of other synonyms. The use of examples anywhere in this specification, including examples of any terms discussed herein, is illustrative only, and in no way limits the scope of the invention so long as the data are processed, sampled, converted, or the like according to the invention without regard for any particular theory or scheme of action.

Figure 1:
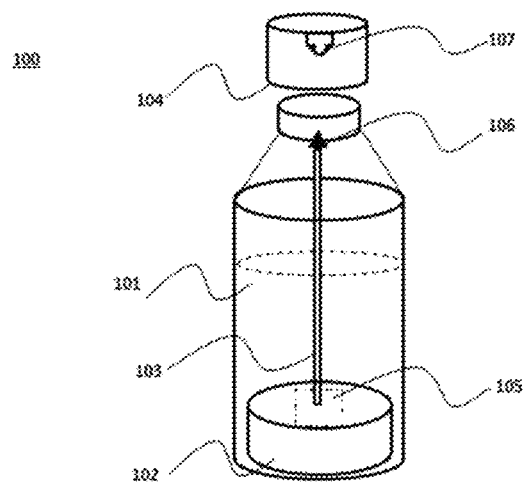
FIG. 1. is a perspective view of a 0.5 liter (L), HDPE, shipping container disposed with a rigid tether between the container cap and a tear-away section of the gas canister.

In an embodiment, (FIG. 1) live-cell shipping container 100 is 0.5 L in volume and made from high-density polyethylene (HDPE). All interior surfaces of the live-cell shipping container 100 are chemically sterilized. Container 100 is filled with a mono culture of *S. cerevisiae*, in an oxygen-saturated slurry of stationary phase media 101, at a concentration of 0.001-5.0 billion cells/ml. Stationary phase media 101 contains no carbon sources available for feeding and maintains yeast in a quiescent state with minimal metabolic activity. Because live yeast retain stores of glycogen they can survive starvation for extended periods (Wilson 2010). The filled container 100 is shipped on water ice to maintain an approximate shipping temperature of 4° C. until the destination is reached. In the embodiment, container 100 enables on-demand feeding with the thermolabile enzyme-substrate pair: vegetable starch and alpha-amylase. Vegetable starch is not biochemically available for consumption by yeast and is supplemented to stationary phase media at the rate of 0.001-1000.0 g/L. Alpha-amylase glycosidase is supplemented to stationary phase media at the rate of 1.0e(−9)-1.0 g/L. The enzyme is activated by increasing the temperature of the shipping container 100 to the temperature range in which the alpha-amylase enzyme active, approximately 30° C., and then maintaining that temperature for about one hour. During this incubation period alpha-amylase depolymerizes starch to glucose and maltose thereby enabling on-demand feeding.

In another aspect of the foregoing embodiment, live-cell shipping container 100 is further disposed with means for supplying nutrient oxygen gas on-demand. Live-cell shipping container 100 includes a gas canister 102 that is affixed to the distal end or bottom of the container 100. The gas canister contains no more than 2.8 grams of $O_2$ yielding 1 L of gas upon release, and 18 PSI at 4° C. In this embodiment the apical surface of gas canister 102 is disposed with a tear-away section 105 that is connected to the basal end of rod 103. The apical end of rod 103 is disposed with a male barb 106 that fits into a corresponding female receptacle 107 located in the cap 104. After the shipping container 100 is filled, it is capped so that the barb 106 and receptacle 107 form a physical tether between the cap 104 and gas canister 102. Removing the cap 104 applies an upward or proximal force to the rod 103 and to the tear-away section 105 of the gas canister 102 thereby releasing the nutrient oxygen gas. In other embodiments the rod 103 need not be connected to the cap 104, but may be disposed with a ring in place of the barb 106 in order to be pulled upon in a proximal direction.

Figure 2:
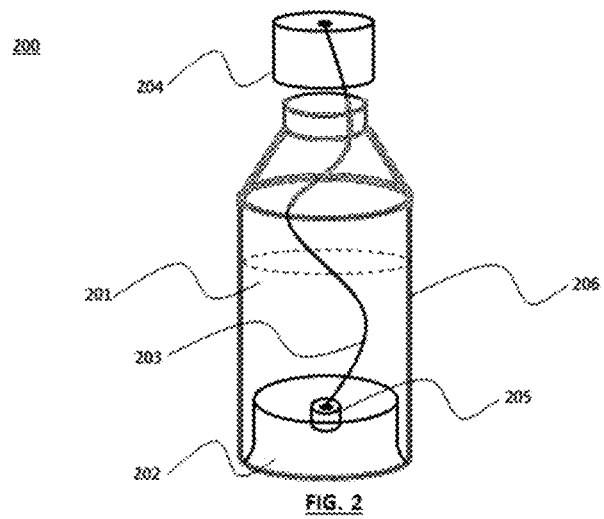
FIG. 2. is a perspective view of a 1 L, polypropylene, shipping container disposed with a flexible tether between the container cap and a plug in the gas canister.

In an alternate embodiment (FIG. 2) live-cell shipping container 200 is 1 L in volume and made from polypropylene (PP). All interior surfaces of shipping container 200 are sterilized by gamma irradiation, and are disposed with a hydrogel coating to prevent cellular attachment. Shipping container 200 is insulated 206 and also provides UV protection. Container 200 is filled with a mono culture of *S.*

*cerevisiae* at a concentration of 0.001-5.0 billion cells/ml in an oxygen-saturated slurry of stationary phase media 201 chilled to a shipping temperature of 4° C. On-demand feeding is enabled by a thermolabile enzyme substrate pair: lactose and beta-galactosidase. Lactose is a disaccharide that is substantially unavailable for consumption by yeast and is supplemented at the rate of 0.001-1000 g/L. Stationary phase media 201 is further supplemented with beta-galactosidase, at a concentration of 1.0e(−9)-1.0 g/L. Some beta-galactosidase enzymes have activity at 25° C. (Hermedia 2007). In this insulated embodiment beta-galactosidase is activated by placing the shipping container in an incubator for sufficient time to increase the temperature of stationary phase media to 25° C. and then maintain that temperature for approximately 1 hour. In other embodiments a sterile heating element or still other means could be used to increase the temperature of stationary phase media 201. Once activated beta-galactosidase cleaves lactose to galactose and glucose thereby enabling on-demand feeding. Live-cell shipping container 200 is further disposed with means for supplying nutrient oxygen gas on-demand. Live-cell shipping container 200 includes a gas canister 202 integrally formed with the base of the shipping container 200. The gas canister 202 contains no more than 5.6 grams of O2 which yields 2 liters of oxygen gas, and 18 PSI at 4° C. The apical surface of the gas canister 202 is disposed with an orifice between 0.01-1.0 cm in diameter and a polypropylene plug 205. In other embodiments the plug could be made from other materials. The plug 205 is connected to the cap 204 by a flexible physical tether 203. The apical end of tether 203 is affixed to the underside of cap 204. Removing cap 204 pulls the plug 205 out of gas canister 202 thereby releasing nutrient oxygen. In other embodiments the flexible tether 203 need not be connected to the cap 204 but may be disposed through the cap 204 or elsewhere with a ring that can be pulled proximally thereby removing the plug 205 from gas canister 202 and enabling on-demand supply of nutrient gas.

Figure 3:
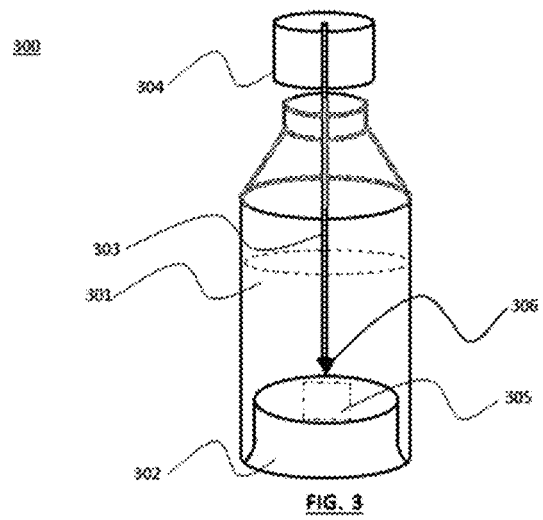
FIG. 3. is a perspective view of a 5 L, PET, shipping container disposed with a puncture rod between the container cap and the gas canister.

In another embodiment (FIG. 3) live-cell shipping container 300 is 5 L in volume and made from polyethylene terephthalate (PET) plastic. All interior surfaces of shipping container 300 are chemically sterilized and are disposed with a hydrogel coating to prevent cellular attachment. Container 300 is filled with a mono culture of *L. delbruckii* at a concentration of 0.001-100 billion cells/ml in an oxygen-saturated slurry of stationary phase media 301. In this embodiment, the *L. delbruckii* strain is a genetic mutant that lacks the lacZ gene. The container 300 is shipped on water ice to maintain an approximate shipping temperature of 4° C. On-demand feeding is enabled by a thermolabile enzyme substrate pair: lactose and a genetic mutant beta-galactosidase that is active at low temperature. Lactose is supplemented at the rate of 0.001-1000 g/L. Stationary phase media 301 is further supplemented with low temperature mutant beta-galactosidase at the rate of 1.0e(−9)-1.0 g/L. The enzyme is activated by increasing the temperature of the shipping container 300 to the temperature range in which the beta-galactosidase is active, approximately 20° C., and then maintaining that temperature for about one hour. During this incubation period the enzyme cleaves lactose to galactose and glucose thereby enabling on-demand feeding. Live-cell shipping container 300 is further disposed with means for supplying nutrient oxygen gas on-demand. Live-cell shipping container 300 includes a gas canister 302 integrally formed with the base of the shipping container 300. The gas canister contains 300 no more than 28 grams of O2 which yields 10 liters of oxygen gas, and 18 PSI at 4° C. The apical surface of gas canister 302 is disposed with a pre-stressed or thin-walled section 305 that is located directly beneath a barb 306. The barb 306 is disposed upon the distal end of a rod or arm 303. The apical end of rod 303 is affixed to the underside of cap 304. Pushing down on the cap 304, or in a distal direction, causes force to be transmitted through the rod 303 distally to the barb 306 which ruptures the pre-stressed section 305 of gas canister 302. In other embodiments the rod 303 need not be affixed to the cap 304 but may be disposed through the cap or alternately beneath the cap 304. In yet further embodiments the rod 303 may actuate the opening of a door or latch rather than cause a puncture to enable on-demand supply of nutrient gas.

Figure 4:
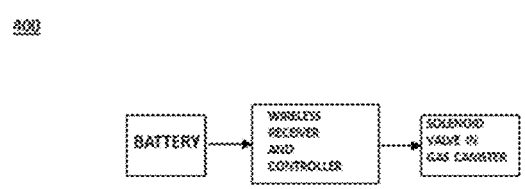
FIG. 4. is a flow diagram depicting the wireless receiver based gas release system disposed within a 50 L, aluminum, shipping container.

In another embodiment (FIG. 4), live cell shipping container 400 is 50 L in volume and made from aluminum. All interior surfaces of shipping container 400 are steam sterilized. Container 400 is filled with a mixed culture of *L. casei* and *L. brevis*, in an oxygen saturated slurry of stationary phase media at a concentration of 0.001-100 billion cells/ml. On-demand feeding is enabled by a thermolabile enzyme substrate pair: isomaltose and isomaltase. Isomaltose, also known as alpha limit dextrose is a disaccharide that is substantially unavailable for consumption by *lactobacillus* and is supplemented at the rate of 0.001-1000 g/L. Stationary phase media 301 is further supplemented with isomaltase enzyme at a concentration of 1.0e(−9)-1.0 g/L. Isomaltase depolymerizes isomaltose to maltose thereby enabling on-demand feeding. On-demand nutrient gas is supplied by a gas canister affixed to the base of the shipping container 400. The gas canister contains no more than 280 grams of O2 which yields 100 L of oxygen gas, and 18 PSI at 4° C. An unobstructed surface of the gas canister is disposed (FIG. 4) with wireless receiver/controller and a battery that are used to open a solenoid valve in the gas canister, and releasing the gas through a diffuser. In another embodiment a piezo-electric valve or other suitable valve could be used. The wireless receiver enables the gas canister to be opened by cell phone or similar device.

Figure 5:
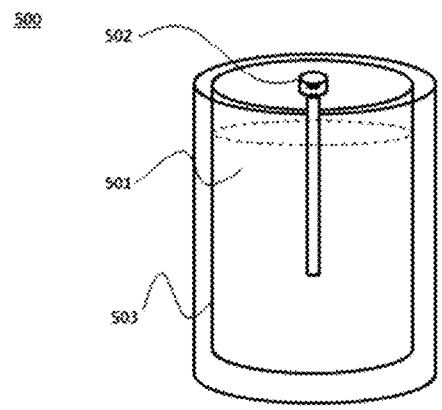
FIG. 5. is a perspective view of a 100 L, stainless steel, shipping container disposed with a disposable PET liner and Sankey valve fitting.

In another embodiment (FIG. 5) live cell shipping container 500 is 100 L in volume and made from stainless steel. Shipping container 500 is disposed with a Sankey valve 502 and with a disposable PET liner 503. All interior surfaces of shipping container 500 are chemically sterilized. Container 500 is filled with a pure culture *S. cerevisiae* at a concentration of 0.001-5.0 billion cells/ml in an oxygen-saturated slurry of stationary phase media 501. On-demand feeding is enabled by supplementing the stationary phase media 501 with a thermolabile enzyme substrate pair: heparin and heparinase. Heparin is a carbohydrate that is substantially unavailable for consumption by yeast and is supplemented at the rate of 0.001-1000 g/L. Stationary phase media 501 is further supplemented with a heparinase enzyme at a concentration of 1.0e(−9)-1.0 g/L. Heparinase is activated by increasing the temperature of shipping container 500 to 20° C. On-demand nutrient gas is supplied by connecting an external nutrient gas source to the Sankey valve 502 by means of a Sankey coupler. Nutrient oxygen gas is pumped into the shipping container 502 without allowing the contents to escape thereby saturating the solution with nutrient gas. In other embodiments an external gas source is used to supply nutrient gas to the shipping container through other kinds of valves and couplers.

Figure 6:
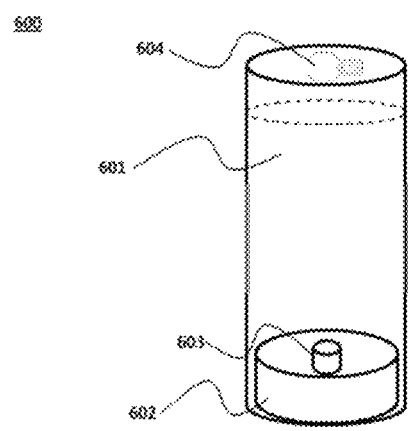
FIG. 6. is a perspective view of a 0.44 L, aluminum, shipping container disposed with a plugged gas canister.

In another embodiment (FIG. 6) shipping container 600 is 0.44 L in volume and made from aluminum. All interior surfaces of shipping container 600 are sterilized by gamma irradiation. Container 600 is filled with a mixed culture of *Pisolithus* and *Glomus* mycorhizzae at a concentration of 0.001-100 billion cells/ml in an oxygen-saturated slurry of stationary phase media 601. On-demand feeding is enabled by supplementing the stationary phase media 601 with the thermolabile enzyme substrate pair: lactose and beta-galactosidase. Lactose is substantially unavailable for consumption by mycorhizzae and is supplemented at the rate of 0.001-1000 g/L. The stationary phase media 601 is further supplemented with a beta-galactosidase enzyme at a concentration of 1.0e(−9)-1.0 g/L. On-demand oxygenation is enabled by a gas canister 602 with an orifice between 0.01-1.0 cm in diameter, sealed with a gelatin plug 603. In other embodiments the plug could be made from other materials. Gas canister 603 contains no more than 2.4 g of $O_2$ which yields 0.88 liters of oxygen gas, and 18 PSI at 4° C. Upon opening the lid 604, gas above the stationary phase media 601 is released followed by evolution of gas still dissolved in the stationary phase media 601. As a result the gelatin plug 603 is exposed to a large depressurization causing it to be expelled from the gas canister 602 orifice.

Figure 7:
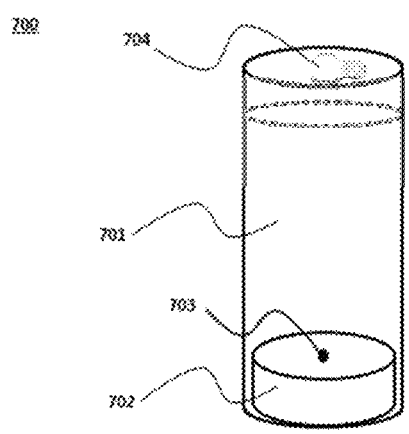
FIG. 7. is a perspective view of a 0.44 L, aluminum, shipping container disposed with an un-plugged gas canister.

In yet another embodiment (FIG. 7) shipping container 700 is 0.44 L in volume and made from aluminum. All interior surfaces of shipping container 700 are chemically sterilized, and disposed with a non-stick hydrogel surface. Container 700 is filled with a mono culture of *Pichia pastoris* at concentration of 0.001-5 billion cells/ml in an oxygen-saturated slurry of stationary phase media 701. On-demand feeding is enabled by supplementing the stationary phase media 701 with the thermolabile enzyme substrate pair: cellulose and cellulase. Cellulose is substantially unavailable for consumption by these cells and is supplemented at the rate of 0.001-1000 g/L. The stationary phase media 701 is further supplemented with cellulase enzyme at a concentration of 1.0e(−9)-1.0 g/L. Cellulase depolymerizes cellulose to monosaccharides glucose, fructose and galactose thereby enabling on-demand feeding. On-demand oxygenation is enabled by a gas canister 702 affixed to the bottom of shipping container 700. Gas canister 702 is disposed with a circular orifice 703 between 0.01-1 cm in diameter. When container 700 is filled with an oxygen saturated slurry of cells and then capped, gas in the container reaches equilibrium between that dissolved in stationary phase media 701, that in the space above the stationary phase media 701 and gas in the space within the gas canister 702. Upon opening the lid 704 the depressurization causes gas to escape from the orifice 703 of gas canister 702 thereby enabling on-demand supply of nutrient gas.

The present invention improves upon the prior art by providing methods and a shipping container for starter cultures that enable on-demand feeding and on-demand supply of nutrient gas to live cells. These improvements provide highly viable starter cultures for a range of organisms used in fermentation wherein an accurate cell count of the initial population is provided and where the number of cells pitched matches the quantity of substrate available enabling efficient, complete and better quality fermentations.

What is claimed is:

1. A method of shipping live cells comprising:
   a. filling a sterile shipping container with live cells in a chilled, liquid media that is saturated with nutrient gas and is without any food source, said cells having reached a stationary growth phase;
   b. adding to the media from step a
      i) a carbon source that is unavailable to the live cells for feeding; and
      ii) an enzyme that is capable of digesting the carbon source at temperatures greater than 4° C.;
   c. affixing an air-tight cap to the shipping container;
   d. transporting said shipping container on water ice or at about 4° C.;
   e. increasing the temperature of the media to activate the enzyme added in step b to digest the carbon source added in step b and provide a food source for the live cells;
   f. releasing nutrient gas from a canister inside the shipping container or supplying nutrient gas to the shipping container from an external gas source;
   g. adding said live cells from step f to a fermentation process.

2. The method of claim 1 wherein the live cells shipped are one species or a mixture of species selected from the group consisting of: fungal cells, bacterial cells, animal cells and plant cells.

3. The method of claim 1 wherein the live cells shipped are genetic mutants.

4. The method of claim 1 wherein an unavailable carbon source is one or a mixture of sources chosen from the group consisting of Agarose, Alginic Acid, Amylose, Amylopectin, Cellulose, Chitin, Chitosan, Chondroitin Sulfates, Dextran, β-Glucans, Glycogen, Hemicellulose, Heparan Sulfate, Heparin, Hyaluronic Acid, Inulin, Isomaltose, Lactose, Lichenen, Pectins, Peptidoglycans, Pullulan, Starch, Trehalose, and Xylan.

5. The method of claim 1 wherein enzymes capable of digesting the unavailable carbon source are one or a mixture of enzymes chosen from the group consisting of Agarase, Alginate Lyase, α-Amylase, β-Amylase, Amyloglucosidase, β-Galactosidade, Cellulase, Chitinase, Chitosanase, Chondroitinases, Dextranase, Driselase, α-Glucosidase, Hemicellulase, Heparinases, Hyaluronidase, Inulinase, Isoamylase, Isomaltase, Lysozyme, Lyticase, Laminarinase, Pectinase, Pectolyase, Pectinesterase, Pullulanase and Xylanase.

6. The method of claim 1 wherein the unavailable carbon sources are one or a mixture of sources chosen from the group consisting of carbohydrates, lipids, proteins, and nucleic acids.

7. The method of claim 1 wherein the enzyme is one or a mixture of enzymes chosen from the group consisting of amylases, lipases, proteases, and nucleases.

8. The method of claim 1 wherein the enzyme is a genetic mutant.

9. The method of claim 1 wherein the nutrient gas in step f is one or a mixture of gases chosen from the group consisting of $O_2$, $N_2$, $H_2$, $CO_2$, $CH_4$, CO and NO.

10. The method of claim 1 wherein nutrient gas is released by pulling upon a physical tether attached to a tear away section in a gas canister inside the shipping container.

11. The method of claim 1 wherein nutrient gas is released by pulling upon a physical tether attached to a plug in an orifice of the gas canister inside the shipping container.

12. The method of claim 1 wherein nutrient gas is released by applying pressure to a puncture rod positioned adjacent to the gas canister inside the shipping container.

13. The method of claim 1 wherein nutrient gas is released by applying pulling pressure or pushing pressure to an arm attached to a door on the gas canister inside the shipping container.

14. The method of claim 1 wherein nutrient gas is released by use of a wireless receiver and battery which open a solenoid valve in the gas canister inside the shipping container.

15. The method of claim 1 wherein nutrient gas is released by use of a wireless receiver and battery which powers a piezoelectric valve in the gas canister inside the shipping container.

16. The method of claim 1 wherein nutrient gas is supplied to the shipping container by connecting an external gas source to a valve on an external surface of the shipping container.

17. The method of claim 1 wherein nutrient gas is released by opening the shipping container, causing rapid depressurization which expels a plug from an orifice in the gas canister inside the shipping container.

18. The method of claim 1 wherein nutrient gas is released by opening the shipping container so that rapid depressurization causes gas to escape from an orifice in the gas canister inside the shipping container.

19. The method of claim 1 wherein the shipping container has one or a combination of the following features: chemically sterilized interior surfaces, nonstick interior surfaces, an insulated, isothermic construction; and opaqueness for ultra violet-protection.

\* \* \* \* \*